United States Patent [19]

Tóth et al.

[11] 4,064,121
[45] Dec. 20, 1977

[54] SUBSTITUTED NITROBENZOPHENONE DERIVATIVES AND A PROCESS FOR THE PREPARATION THEREOF

[75] Inventors: Edit Tóth; József Törley; Eva Palosi; Szaboles Szeberenyi; Laszlo Szporny; Sandor Görög; Csilla Mészaros, all of Budapest, Hungary

[73] Assignee: Richter Gedeon Vegyeszeti Gyar Rt., Budapest, Hungary

[21] Appl. No.: 603,855

[22] Filed: Aug. 12, 1975

Related U.S. Application Data

[62] Division of Ser. No. 485,701, July 3, 1974, Pat. No. 3,957,777.

[30] Foreign Application Priority Data

July 26, 1973  Hungary .................................. RI 517

[51] Int. Cl.² ................. C07D 225/02; C07D 211/14; C07D 707/08
[52] U.S. Cl. .............................. 260/239 B; 260/293.8; 260/326.5 J; 260/239 BE
[58] Field of Search ...................... 260/239 B, 326.5 J, 260/293.8, 239 BE

[56] References Cited

U.S. PATENT DOCUMENTS

| 3,202,665 | 8/1965 | Metlesics | 260/293.79 |
| 3,975,390 | 8/1976 | Toth et al. | 260/239 B |

OTHER PUBLICATIONS

Barker et al. II, Chem. Abs. 81, 25669k (1974).
Louden et al., Chem. Abs. 44, 4888a (1950).
Louden et al. II, Chem. Abs. 52, 8153a (1957).
Barker et al., Chem. Abs. 78, 16198 (1972).
Koelling et al., Chem. Abs. 81, 135774 (1974).

*Primary Examiner*—Donald G. Daus
*Assistant Examiner*—Mark L. Berch
*Attorney, Agent, or Firm*—Karl F. Ross

[57] ABSTRACT

New compounds of the general formula (I),

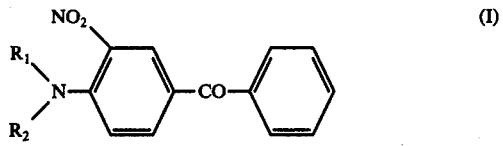

wherein
$R_1$ and $R_2$ each stand for a saturated or unsaturated, straight-chained or branched alkyl group, an aralkyl group, a saturated or unsaturated cycloalkyl group or an aryl group, or
$R_1$ and $R_2$ together with the adjacent nitrogen atom may form an optionally substituted heterocyclic group optionally containing a further oxygen or nitrogen hetero atom, but if $R_1$ stands for methyl, $R_2$ may only stand for a group other than methyl, are prepared by reacting a compound of the general formula

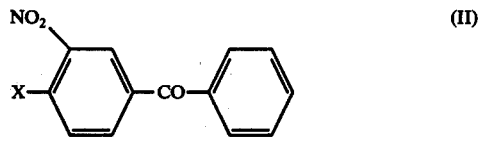

wherein X stands for halogen, with a secondary amine of the general formula (III),

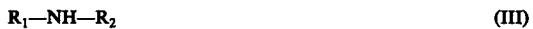

wherein $R_1$ and $R_2$ each have the same meanings as defined above.

The new compounds of the general formula (I), as well as their pharmaceutical acceptable acid addition salts or quaternary ammonium salts are active primarily in the induction of liver microsomal enzyme, but they also possess antipyretic activity.

4 Claims, No Drawings

SUBSTITUTED NITROBENZOPHENONE DERIVATIVES AND A PROCESS FOR THE PREPARATION THEREOF

This is a division of application Ser. No. 485,701, filed July 3, 1974, now U.S. Pat. No. 3,957,777.

This invention relates to new benzophenone derivatives containing a 3-nitro-4-tert.-amino group, to acid addition salts and quaternary ammonium salts thereof, furthermore to a process for the preparation of such compounds.

The compounds according to the invention correspond to the general formula (I),

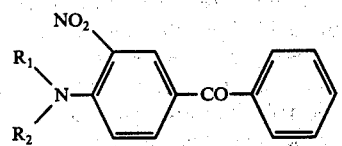

wherein
$R_1$ and $R_2$ each stand for a saturated or unsaturated, straight-chained or branched alkyl group, an aralkyl group, a saturated or unsaturated cycloalkyl group or an aryl group, or $R_1$ and $R_2$ together with the adjacent nitrogen atom may form an optionally substituted heterocyclic group optionally containing a further oxygen or nitrogen hetero atom, but if $R_1$ stands for methyl, $R_2$ may only stand for a group other than methyl.

$R_1$ and $R_2$ represent preferably a saturated or unsaturated, straight-chained or branched $C_{1-18}$ alkyl group (e.g. an alkyl, alkenyl, alkynyl or alkadienyl group), more preferably a $C_{1-10}$ group, such as methyl, ethyl, propyl, allyl, butyl, isobutyl, pentyl, isopentyl, hexyl, 1-octen-7-yl, nonyl or decyl group. The aralkyl group is preferably an aryl-$C_{1-4}$ alkyl group, more preferably a phenyl-$C_{1-4}$ alkyl group, e.g. benzyl, phenethyl, 1-naphthylethyl or 3-phenyl-propyl group. The saturated or unsaturated cycloalkyl group may be, for example, a cycloalkyl, cycloalkenyl cycloalkynyl or cycloalkadienyl group, preferably a $C_{3-8}$ monocyclic group, such as cyclopropyl, cyclopentyl, cyclohexyl, cyclohexenyl, cycloheptyl, etc. group. The aryl group is preferably a phenyl group or a substituted phenyl group of the general formula $C_6H_4X$, wherein X may stand for halogen (e.g. fluorine, chlorine, bromine or iodine), alkyl as listed above, e.g. methyl ethyl, hexyl or decyl, alkoxy, e.g. methoxy, ethoxy, propoxy, butoxy, isobutoxy or decyloxy, or the like.

$R_1$ and $R_2$ may form together a saturated or unsaturated alkylene group containing preferably 4 to 10, more preferably 4 to 7 carbon atoms, which, together with the adjacent nitrogen atom, may form a heterocyclic group, such as a pyrrolo, pyrrolidino, piperidino, azepino or heptamethyleneimino group. Alternatively, $R_1$ and $R_2$ may form together a nitrogen- or oxygen-containing saturated or unsaturated alkylene group, which, together with the adjacent nitrogen atom, may form a heterocyclic group containing more than one hetero atoms, such as a morpholino, imidazolo, indolo, benzimidazolo or 1,4-benzisoxazolo group. These heterocyclic groups may be saturated or unsaturated and may have a substituent, preferably an alkyl group, on either of the atoms constituting the ring.

$R_3$ may represent, as an acyl group derived from a $C_{1-18}$ carboxylic acid, e.g. formyl, acetyl, propionyl, butynyl, isobutynyl, valeryl, caproyl, pivaloyl, or palmitoyl group, an acyl group derived from an unsaturated aliphatic carboxylic acid, e.g. acryloyl, propiolyl, methacryloyl, crotonoyl, etc. group, or an acyl group derived from a carbocyclic carboxylic acid, e.g. toluoyl or benzoyl group. These acyl groups may be optionally substituted e.g. with a halogen, an alkyl group as defined above, an alkoxy group. etc.

The compounds of the general formula (I) possess valuable pharmacological properties. According to our experiments these compounds are active primarily in the induction of liver microsomal enzyme, but they also possess antipyretic activity. As reference substances, phenobarbital and phenacetine were used in the experiments. The pharmacological tests were carried out as follows:

To investigate the enzyme inductive effect, Wistar female rats, each weighing 40 to 50 g. were treated with pure solvent, or with a dosage of 60 mg./kg. of phenobarbital or the compound to be tested, respectively. 24 hours after this treatment 40 mg./kg. of hexobarbital were administered intravenously into the animals. The reduction of the elimination period and the liver enzyme induction was expressed as the shortening of the duration of sleeping.

To test the antipyretic effect, a 15% yeast suspension was administered to male rats each weighing 180 ±10 g. No food was given to the animals, they could consume, however, arbitrary amount of water. 16 hours after the administration of yeast the rectal body temperature of the animals was taken, and the animals were treated with pyrago in an intravenous dosage of 50 M bact./animal. The compound to be tested was administered orally into the animals, thereafter the change in rectal temperature both for the treated and the control animals was recorded for 5 hours, using an "Elab" type electrothermometer. Phenacetine, used as reference substance, and the compounds of the invention were administered in dosages of 40 mg./kg. body weight.

The results of the above tests are presented in Tables 1 and 2. In these tables the following abbreviations are used:

$B_2$ = 3-nitro-4-morpholino-benzophenone
$B_9$ = 3-nitro-4-(N,N-diisobutylamino)-benzephenone
$B_{11}$ = 3-nitro-4-(N-methyl-piperazino)-benzophenone ethobromide.
p.o. = per os
S.E. = standard error Table 1

| | Inductive effect | |
|---|---|---|
| Compound | Dosage p.o. mg./kg. | Mean duration of sleeping ± S.E., minutes |
| Control | — | 19.4 ± 1.88 |
| Phenobarbital | 60 | 14.2 ± 1.88* |
| $B_2$ | 60 | 14.6 ± 1.65* |

*p>0.05 (below a significance level of 5 %)

Table 2

| | Antipyretic activity |
|---|---|
| Compound | Decrease of temperature, ° C |
| Phenacetine | −1.1 |
| $B_9$ | −1.0 |
| $B_{11}$ | −1.1 |

The anticonvulsive effect was tested on spasm induced by electroshock, tetracor or strychnin, respectively, the muscle relaxation was examined by the rotarod test, while the sedative effect was tested by determining the amount of sodium barbital which does not cause hypnosis.

Inductive effect: $LD_{50}$ mg./kg. p.o.: phenobarbital: 240.0; $B_2$: 1200.0.

Antipyretic activity: $LD_{50}$ mg./kg. p.o.: phenacetine: 2405; $B_9$: above 3000; $B_{11}$: above 3000.

As it appears from the data of Table 1, the inductive effect of compound $B_2$ is the same as that of phenobarbital. Phenobarbital is, however, known to exert significant effects on the central nervous system, which manifests at the test animals in ataxia, sedatio and anticonvulsive effect. In contrast, compound $B_2$ has no effect on the central nervous system in the dosage utilized.

Compounds $B_9$ and $B_{11}$ are similar in antipyretic activity to phenacetine. The compounds of the invention have, however, more favourable therapeutical indices and exert no harmful effect on the kidneys in the pharmacological tests.

The compounds of the invention can be used as pharmaceuticals, and they also are valuable starting substances for the syntheses of pharmacologically active agents.

The new compounds of the general formula (I), wherein $R_1$ and $R_2$ each have the same meanings as defined above, are prepared according to the invention by reacting a 3-nitro-benzophenone of the general formula (II)

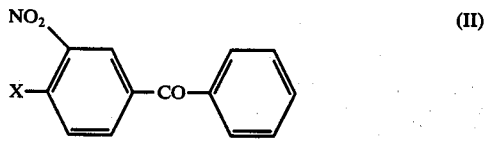

wherein X stands for halogen, with a secondary amine of the general formula (III),

TI $R_1$ — NH — $R_2$              (III)

wherein $R_1$ and $R_2$ each have the same meanings as defined above. If desired, the thus-obtained free bases are converted into their acid addition salts or quaternary ammonium salts, or the free bases can be liberated from the compounds obtained in the form of their acid addition salts.

The starting compounds of the general formula (II) can be prepared by the method of Maron and Fox (Ber. 2777/1914/).

The reaction is carried out preferably in an organic solvent, in the presence of a base capable of binding the acid liberated in the reaction.

As solvent, e.g. hydrocarbons, such as petrol, benzene, or toluene, halogenated hydrocarbons, such as chloroform, ethers, such as dioxane, alcohols, such as ethanol, esters, such as ethyl acetate, etc. can be used.

As acid binding agent preferably inorganic bases or tertiary organic bases are used. An excess of the amine of the general formula (III) may also act as acid binding agent.

If the amine of the general formula (III) or a tertiary organic base used as hydrogen halide binding agent is applied in excess, it may serve simultaneously as the solvent medium for the reaction.

The reaction is carried out at temperatures ranging from 20° C to the boiling point of the solvent, preferably at a temperature between 60° C and 140° C. The progress of the reaction can be monitored easily be thin layer chromatography.

When the reaction has been completed the obtained product is isolated. The reaction mixture can be processed e.g. by pouring the mixture onto water, and separating the product by solvent extraction. The organic phase is washed with water until halogen-free, the solution is dried, and the solvent is distilled off. One may also proceed by precipitating the product, filtering, washing with water until halogen-free, and drying. The crude product can be purified by treatment with an appropriate solvent and/or by crystallization.

The new compounds of the general formula (I) can be converted into their acid addition salts formed with mineral or organic acids. The salt-forming acids include e.g. hydrochloric acid, hydrobromic acid, sulphuric acid, phosphoric acid, methanesulphonic acid, ethanesulphonic acid, acetic acid, lactic acid, oxalic acid, fumaric acid, maleic acid, tartaric acid, citric acid, succinic acid, amygdalic acid, benzoic acid, salicylic acid and phenylacetic acid.

If desired, the new compounds of the general formula (I) can be converted into their quaternary ammonium salts by reacting them with a saturated or unsaturated lower alkylhalide, lower alkylsulphate or benzyl halide.

The acid addition salts and quaternary salts of the compounds of the general formula (I) can be converted into the free bases by known methods. The obtained free bases can be converted into other salts, if desired.

The compounds according to the invention can be administered to the patients in pharmaceutically active but nontoxic dosages. The actual amount of the active agent to be administered depends on the pharmaceutical effect to be attained, moreover on the method of treatment, as well as on the general condition and sensitivity of the patient to be treated.

The effective dosage can be administered either in subdivided form several times a day, or in retard form.

The pharmacologically active compounds of the invention can be used in the therapy in the form of pharmaceutical compositions. Such compositions suitable for enteral, parenteral or topical administration may contain the new compounds according to the invention in admixture with solid or liquid, organic or inorganic, pharmaceutically acceptable carriers which do not react with the active agents. These carriers include e.g. water, alcohols, gelatine, propylene glycol, vegetable oils, cholesterol, starch, lactose, talc, gum, magnesium stearate, etc. If desired, the pharmaceutical products can be sterilized.

The pharmaceutical products may contain auxiliary agents, such as preserving, stabilizing, wetting or emulsifying agents, solubilizing substances, salts or buffers to modify the osmotic pressure, etc. These compositions may contain the compounds of the general formula (I) in combination with other therapeutically active agents.

The pharmaceutical compositions are prepared by methods well known in the art. Thus, for example, the injectable compositions are prepared by dissolving an acid addition salt or quaternary ammonium salt of the active agent in pyrogen-free physiological saline solution or in bidistilled water, optionally sterilizing the solution, and filling into ampoulles under sterile conditions.

The invention is elucidated in detail by the aid of the following non-limiting Examples.

EXAMPLE 1

3-Nitro-4-(N.N-diisobutylamino)-benzophenone

A mixture of 26 g of 3-nitro-4-chloro-benzophenone, 20 ml. of ethanol and 35 ml. of diisobutylamine is heated to 80° to 85° C under stirring, and the reaction mixture is kept at this temperature for 6 hours. When the reaction is over the ethanol is distilled off under reduced pressure, and 260 ml. of petroleum ether (b.p.: 40° to 100° C) are added to the solid residue. The separated diisobutylamine hydrochloride is removed by filtration, the filtrate is evaporated, and the residue is recrystallized from ethanol. 32.7 g. of 3-nitro-4-(N,N-diisobutylamino)-benzophenone are obtained, m.p.: 80°–81° C.

Analysis for $C_{21}H_{26}N_2O_3$. Calculated: C 71.16 % H 7.39 % N 7.90 %, Found: C 71.34 % H 7.35 % N 7.99 %.

I.R. spectrum: characteristic bands appear as 700, 730, 830, 870, 1320, 1525, 1650, 2880, 2920, 2940, and 2960 cm$^{-1}$.

U.V. spectrum: $_{max.}{}^{EtOH}$ 252, 345, 410 nm.

EXAMPLE 2

3-Nitro-4-(N,N-di-n-amylamino)-benzophenone

A mixture of 9.12 g. of 3-nitro-4-chloro-benzophenone, 11 g. of di-n-amylamine and 10 ml. of benzene is refluxed for 40 minutes with stirring. The mixture is allowed to cool and diluted with 140 ml. of benzene. The organic base is washed with water until chloride-free. The benzene phase is dried over anhydrous magnesium sulphate, filtered, and evaporated under reduced pressure. 13.3 g. of 3-nitro-4-(N,N-di-n-amylamino)-benzophenone are obtained as a viscous, oily residue.

Analysis for $C_{23}H_{30}N_2O_3$: Calculated: C 72.22 % H 7.91 % N 7.32 %, Found: C 72.11 % H 7.72 % N 7.40 %.

I.R. spectrum: characteristic bands appear at 700, 740, 800, 870, 1320, 1530, 1650, 2880, 2860, 2940, and 2960 cm$^{-1}$.

U.V. spectrum: $_{max.}{}^{EtOH}$ 252, 344, 410 nm.

EXAMPLE 3

3-Nitro-4-(N-ethyl-N-cyclonemylamino)-benzophenone 13 g. of 3-nitro-4-chloro-benzophenone are reacted with 15 ml. of N-ethyl-N-cyclohexylamine as described in Example 2. The crude product is recrystallized from n-hexane to yield 15.3 g. of para, crystalline 3-nitro-4-(N-ethyl-N-cyclohexylamino)-benzophenone; m.p: 91.5–92° C.

Analysis for $C_{21}H_{24}N_2O_3$: Calculated: C 71.57 % H 6.86 % N 7.95 %, Found: C 71.65 % H 6.93 % N 7.82 %.

I.R. spectrum: characteristic bands appear at 710, 730, 800, 860, 1310, 1530, 1650, 2860, and 2940 cm$^{-1}$.

U.V. spectrum: $_{max.}{}^{EtOH}$ 252, 346 nm.

EXAMPLE 4

3-Nitro-4-(N-methyl-N-octylamino)-benzophenone

A mixture of 9.23 g. of 3-nitro-4-chloro-benzophenone, 10 ml. of ethanol and 10.3 g. of N-methyl-N-octylamine is stirred at 80° to 85° C for 30 minutes, and then the mixture is poured onto 100 ml. of ice water. The aqueous phase is extracted with 2x75 ml. of benzene. The benzene phases are combined, washed with distilled water with chloride-free, dried over anhydrous magnesium sulphate, filtered, and evaporated in vacuo. 11.57 g. of 3-nitro-4-(N-methyl-N-octylamino)-benzophenone are obtained in the form of an oily residue. On the basis of thin layer chromatographical examination, a pure, uniform product is obtained.

Analysis for $C_{22}H_{28}N_2O_3$: Calculated: C 71.71 % H 7.66 % N 7.60 %, Found: C 71.65 % H 7.58 % N 7.66 %.

I.R. spectrum: characteristic bands appear at 700, 740, 820, 875, 1320, 1530, 1650, 2860, and 2940 cm$^{-1}$.

U.V. spectrum: $_{max.}{}^{EtOH}$ 248, 340, 406 nm.

EXAMPLE 5

3-Nitro-4-(N-ethyl-N-phenylamino)-benzophenone 30.6 g. of 3-nitro-4-bromo-benzophenone are reacted with 23.5 ml. of N-ethylaniline as described in Example 2. The obtained 34 g. of crude 3-nitro-4-(N-ethyl-N-phenylamino)-benzophenone are recrystallized from ethanol to yield 27.68 g. of pure, crystalline product, melting at 99.5° C.

Analysis for $C_{21}H_{18}N_2O_3$: Calcuted: C 72.82 % H 5.24 % N 8.09 %, Found: C 72.91 % H 5.31 % N 8.10 %.

I.R. spectrum: characteristic bands appear at 700, 710, 740, 800, 870, 1320, 1530, 1650, 2920, and 2980 cm$^{-1}$.

U.V. spectrum: $_{max.}{}^{EtOH}$ 252, 352 nm.

EXAMPLE 6

3-Nitro-4-(N-methyl-N-benzylamino)-benzophenone 26 g. of 3-nitro-4-chloro-benzophenone are reacted with 26.84 ml. of N-methyl-N-benzylamine as described in Example 2. The benzene solution is evaporated, and the residue is suspended in n-hexane. The solids are filtered off and dried to yield 32.9 g. of 3-nitro-4-(N-methyl-N-benzylamino)-benzophenone; m.p.: 99.5° C.

Analysis for $C_{21}H_{18}N_2O_3$: Calculated: C 72.82 % H 5.24 % N 8.09 %, Found: C 72.94 % H 5.16 % N 7.99 %.

I.R. spectrum: characteristic bands appear at 700, 730, 740, 820, 860, 1320, 1530, 1650 cm$^{-1}$.

U.V. spectrum: $_{max.}{}^{EtOH}$ 248, 334, 408 nm.

EXAMPLE 7

3-Nitro-4-piperidino-benzophenone 15 ml. of piperidine are added at once to 13 g. of 3-nitro-4-chloro-benzophenone under stirring. Due to the highly exothermic reaction the mixture warms to 98° to 100° C within 4 to 5 minutes, thereafter piperidine hydrochloride starts to separate from the homogeneous reaction mixture. The mixture is stirred for 10 minutes at 98° to 100° C, thereafter cooled, the product is triturated with 30 ml. of n-hexane, and filtered. The crystalline substance is washed on the filter with 2×30 ml. of n-hexane, suctioned well, and suspended several times in distilled water to remove piperidine hydrochloride. The obtained product is dried until constant weight. 15.5 g. of crystalline 3-nitro-4-piperidino-benzophenone are obtained; m.p.: 77° C.

Analysis for $C_{18}H_{18}N_2O_3$: Calculated: C 69.66 % H 5.85 % N 9.03 %, Found: C 69.53 % H 5.72 % N 8.98 %.

I.R. spectrum: characteristic bands appear at 710, 735, 830, 870, 1315, 1520, 1650, 2840, 2940 cm$^{-1}$.

U.V. spectrum: $_{max.}{}^{EtOH}$ 250, 340, 410 nm.

EXAMPLE 8

3-Nitro-4-piperidino-benzophenone

A mixture of 26 g. of 3-nitro-4-chloro-benzophenone, 52 ml. of benzene and 8.7 g. of pyridine is heated to 80° C, thereafter a solution of 8.5 g. of piperidine in 10 ml. of benzene are added at once. The reaction mixture warms to 83° C. After 10 minutes the mixture is cooled to room temperature, diluted with 100 ml. of benzene, and the organic phase is washed with distilled water until chloride-free. The benzene solution is dried over anhydrous magnesium sulphate, filtered, and evaporated to dryness under reduced pressure. 30.7 g. of crystalline 3-nitro-4-piperidine-benzophenone are obtained, the physical constants of which are the same as listed in Example 7.

EXAMPLE 9

3-Nitro-4-pyrrolidino-benzophenone

3Nitro-4-chloro-benzophenone is reacted with pyrrolidine as described in Examples 7 or 8 obtain 3-nitro-4-pyrrolidino-benzophenone with a yield of 95 %. The crystalline product melts at 89.5° – 90.5° C.

Analysis for $C_{17}H_{16}N_2O_3$: Calculated: C 68.90 % H 5.44 % N 9.45 %, Found: C 68.81 % H 5.37 % N 9.31 %.

I.R. spectrum: Characteristic bands appear at 705, 745, 820, 870, 1320, 1540, 1650, 2880, 2960 cm$^{-1}$.

U.V. spectrum: $_{max.}^{EtOH}$ 248, 338, 406 nm.

EXAMPLE 10

3-Nitro-4-heptamethyleneimino-benzophenone

3-Nitro-4-chloro-benzophenone is reacted with heptamethyleneimine as described in Example 7 to obtain 3-nitro-4-heptamethyleneimino-benzophenone with a yield of 96 %. The product melts at 91° C.

Analysis for $C_{20}H_{22}N_2O_3$: Calculated: C 70.98 % H 6.55 % N 8.28 %, Found: C 70.89 % H 6.58 % N 8.20 %.

I.R. spectrum: characteristic bands appear at 710, 730, 830, 860, 1310, 1540, 1650, 2860, and 2930 cm$^{-1}$.

U.V. spectrum: $_{max.}^{EtOH}$ 344, 408 nm.

EXAMPLE 11

3-Nitro-4-morpholino-benzophenone

3-Nitro-4-chloro-benzophenone is reacted with morpholine as described in Example 7 to obtain 3-nitro-4-morpholino-benzophenone with a yield of 98 %. The product melts at 103° C.

Analysis for: $C_{17}H_{16}N_2O_4$: Calculated: C 65.37 % H 5.16 % N 8.97 %, Found: C 65.40 % H 5.10 % N 8.77 %.

I.R. spectrum: characteristic bands appear at 700, 735, 800, 875, 1315, 1520, 1650, 2860, 2900, 2940, and 2980 cm$^{-1}$.

U.V. spectrum: $_{max.}^{EtOH}$ 248, 328, 406 nm.

EXAMPLE 12

3-Nitro-4-(N-methyl-piperazino)-benzophenone

N-methyl-piperazine is reacted with 3-nitro-4-chloro-benzophenone as described in Example 7 or 8 to obtain 3-nitro-4-(N-methyl-piperazino)-benzophenone with a yield of 90 %. The product melts at 94° C.

Analysis for $C_{18}H_{19}N_3O_3$: Calculated: C 66.44 % H 5.89 % N 12.92 %, Found: C 66.28 % H 5.83 % N 12.79 %.

I.R. spectrum: characteristic bands appear at 705, 740, 830, 860, 1295, 1525, 1650, 2780, 2805, 2840, and 2960 cm$^{-1}$.

U.V. spectrum: $_{max.}^{EtOH}$ 250, 331, 406 nm.

The above base is dissolved in methanol and an isopropanol solution of hydrochloric acid is added: This way 3-nitro-4-(N-methyl-piperazino) benzophenone hydrochloride is obtained, m.p.: 248.5°–249° C.

The methanol solution of the free base is treated with the methanol solution of fumaric acid to yield the corresponding fumarate salt; m.p.: 184.5°–185.5° C.

EXAMPLE 13

3-Nitro-4-(N-methyl-piperazino)-benzophenone ethobromide

A mixture of 4.88 g. of 3-nitro-4-(N-methyl-piperazino)-benzophenone, 78 ml. of acetone and 9.8 g. of ethyl bromide is refluxed for 16 hours. The quaternary salt separates from the reaction mixture in crystalline form. The reaction mixture is cooled, the crystals are filtered off, washed with acetone, and dried. 6.1 g. of 3-nitro-4-(N-methyl-piperazino)-benzophenone ethobromide are obtained; m.p.: 230°–231° C.

What is claimed is:

1. A compound of the formula:

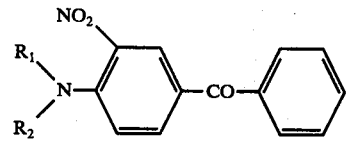

or a pharmaceutically acceptable acid addition or quaternary ammonium salt selected from the group consisting of saturated or unsaturated lower alkyl halides, lower alkyl sulfates and benzyl halides thereof, wherein $R_1$ and $R_2$ form together a heterocyclic group selected from the group which consists of piperidino, pyrrolidino and heptamethyleneimino.

2. The compound defined in claim 1 which consists of 3-nitro-4-piperidino-benzophenone, or pharmaceutically acceptable acid addition or quaternary ammonium salts thereof.

3. The compound defined in claim 1 which consists of 3-nitro-4-pyrrolidino-benzophenone, or pharmaceutically acceptable acid addition or quaternary ammonium salts thereof.

4. The compound defined in claim 1 which consists of 3-nitro-4-heptamethyleneimino-benzophenone, or pharmaceutically acceptable acid addition or quaternary ammonium salts thereof.

* * * * *